United States Patent [19]

Allen

[11] Patent Number: 4,895,727
[45] Date of Patent: Jan. 23, 1990

[54] PHARMACEUTICAL VEHICLES FOR EXHANCING PENETRATION AND RETENTION IN THE SKIN

[75] Inventor: Larry M. Allen, Denver, Colo.

[73] Assignee: Chemex Pharmaceuticals, Inc., Denver, Colo.

[21] Appl. No.: 730,682

[22] Filed: May 3, 1985

[51] Int. Cl.⁴ ............... A61K 33/32; A61K 31/315; A61K 31/56; A61K 31/05

[52] U.S. Cl. ............................ 424/642; 514/169; 514/494; 514/733; 514/734; 514/736; 514/946; 514/947

[58] Field of Search ............... 424/145, 642; 514/736, 514/733, 734, 946, 947, 169, 494

[56] References Cited

U.S. PATENT DOCUMENTS

| | | | |
|---|---|---|---|
| 2,087,162 | 7/1937 | Moore | 424/145 X |
| 4,261,982 | 4/1981 | Luedders et al. | 514/29 |
| 4,349,536 | 9/1982 | Hausler | 424/145 X |
| 4,440,777 | 4/1984 | Zupan | 514/946 X |
| 4,469,684 | 9/1984 | Huggins et al. | 514/29 |

OTHER PUBLICATIONS

Smart, C. R. MD., et al., "Clinical Experience with Nordihydroguaiaretic Acid", J. Rocky Mountain Medical, Nov. 1970, pp. 39-43.

Primary Examiner—John S. Maple
Attorney, Agent, or Firm—Kenyon & Kenyon

[57] ABSTRACT

This invention is a method of inducing a reservoir effect in skin and mucous membranes so as to enhance penetration and retention and reduce transdermal flux of topically applied therapeutic and cosmetic pharmacologically active agents. The invention also relates to topical treatment methods involving such reservoir effect enhancers, and to pharmaceutical compositions containing them.

30 Claims, 1 Drawing Sheet

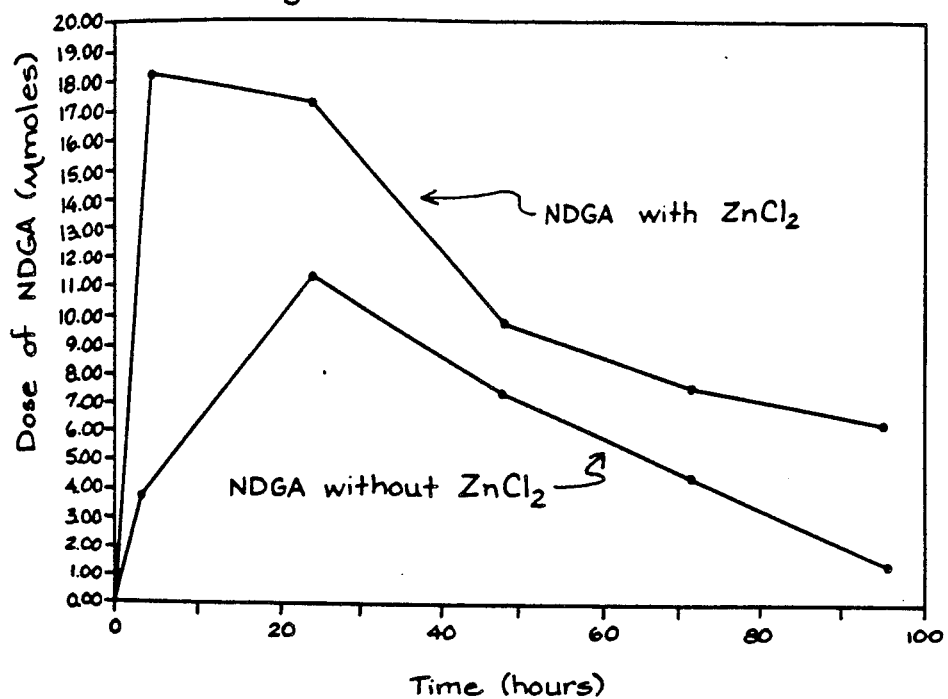

PHARMACEUTICAL VEHICLES FOR EXHANCING PENETRATION AND RETENTION IN THE SKIN

FIELD OF THE INVENTION

Method of inducing reservoir effect in skin and mucous membranes so as to increase penetration and residence time of pharmacologically active agents therein.

BACKGROUND OF THE INVENTION

There are many localized disease conditions which are effectively treated by topical application of suitable physiological agents. In order for such treatments to be maximally effective, it is necessary that as much of the pharmacologically active agent as possible be absorbed into the skin where it can make contact with the disease condition in the dermal tissues without being lost by rubbing off on clothing or evaporation. At the same time, the agent must not penetrate so effectively through the skin as to be rapidly lost to the lymphatic and vascular circulatory systems. This latter factor is especially important when the pharmacologically active agent is toxic when used systemically.

The ideal vehicle for topically applied pharmaceuticals is therefore one which can produce a "reservoir effect" in the skin or mucous membranes to which the topical treatment is applied. This "reservoir effect" is defined as an enhancement of the skin or membrane's ability to both absorb and retain pharmacologically active agents, i.e., to increase skin or membrane residence time decrease drug transit time and reduce transdermal flux.

A number of compounds are known to enhance the ability of pharmacologically active agents to penetrate the skin and mucous membranes, for example, N-bis-azacyclopentan-2-onyl-alkanes, 1-substituted azacycloheptan-2-ones and higher alkyl-substituted azacyclopentan-2-ones, as well as dimethylsulfoxide and lower alkyl sulfoxides. These compounds, however, have the disadvantage of allowing rapid systemic dispersion of the pharmacologically active agents away from the localized site of pathology. Many topical medicaments, such as the retinoids used in the treatment of acne, and methotrexate, used in the treatment of psoriasis, are systemically toxic. The retinoids, for example, are known to cause damage to unborn fetuses. Thus, there is a need for a method of enhancing the ability of such medicaments to penetrate into the skin or mucous membrane so that a lesser total dosage may be used, while at the same time retarding their ability to move from the skin to the interior of the body.

The problem posed by the paradoxical requirement that a systemically toxic topical medicament be efficiently absorbed into, but not through, the skin, has heretofore gone unrecognized. There have been no vehicle additives available to the pharmacological industry which act to enhance the "reservoir capacity" of the skin and mucous membranes so that the amount of pharmacologically active agents reaching and being retained at the site of localized pathologies is maximized.

SUMMARY OF THE INVENTION

This invention is a method for inducing a reservoir effect in skin and mucous membranes so as to enhance penetration and retention of topically applied pharmacologically active therapeutic and cosmetic agents therein. The invention also relates to topical treatment methods involving such reservoir effect enhancers, and to pharmaceutical compositions containing them.

The additives of this invention are water-soluble zinc-containing compounds, preferably zinc halide, zinc sulfate, zinc nitrate, zinc acetate, and/or zinc stearate, and most preferably zinc chloride.

The pharmacologically active agents with which the water-soluble zinc-containing compounds are used are preferably those containing hydroxyl, oxo, sulfhydryl, amine, carboxyl, and other anionic groups in configurations which readily allow complexation or chelation with zinc ions.

In inducing a reservoir effect in the skin and mucous membranes to reduce transdermal flux so that drugs are absorbed and retained therein in larger amounts for longer periods of time than has heretofore been possible, the water-soluble zinc-containing compounds of this invention act as potentiators for the pharmacologically active agents. Potentiation is defined as overcoming or reducing undesirable effects such as systemic toxicity and extending the range of effectiveness of the pharmacologically active agent, or both.

DESCRIPTION OF THE DRAWING

The drawing is a graph of test results showing the skin reservoir effect achieved by the method of this invention utilizing nordihydroguaiaretic acid with zinc chloride, as compared to the same compound without zinc chloride. The nordihydroguaiaretic acid was labelled with carbon-14 for radiotracer analysis. The graph shows immediate absorption and longer retention of larger amounts of the nordihydroguaiaretic acid with zinc chloride present than without. The availability of nordihydroguaiaretic acid, a lipoxygenase inhibitor, to therapeutically act upon localized pathologies, both with and without added zinc chloride, is measured by the areas under the respective curves. It is apparent that skin bioavailability is greatly enhanced in the presence of a zinc-containing compound. The drug flux rate can be calculated as a function of the area under the curve by dividing this area by dose. As is apparent, drug flux rate is substantially decreased over the entire dosage range by the addition of zinc chloride.

DETAILED DESCRIPTION OF THE INVENTION

The zinc-containing compounds of this invention are generally any water-soluble organic or inorganic zinc salts which dissociate in the topical vehicle so as to provide zinc ions for complexation or chelation with the pharmacologically agents present in the vehicle. Examples of suitable zinc-containing compounds are zinc halide, zinc sulfate, zinc nitrate, zinc acetate, and/or zinc stearate. The most preferred zinc-containing compound is zinc chloride.

Such water-soluble zinc-containing compounds may be prepared by means known to the art, and many are commercially available.

The topical preparations of this invention having enhanced reservoir inducing capacities may be prepared by mixing a water-soluble zinc-containing compound into the pharmaceutical preparation or vehicle in which a reservoir-inducing capacity is to be created by means known to the art so as to promote complexation or chelation of the pharmacologically active agents therein with zinc ions. The presence of other metallic ions which would unfavorably compete with zinc for complexation or chelation sites is to be avoided. The zinc salt can also be mixed with the pharmacologically active agent to form a chelate or complex which is then incorporated into the pharmaceutical carrier.

The zinc-containing compounds are preferably present in an equimolar ratio with the pharmacologically active agents, so as to cause maximum complexation or chelation. Where stratum corneum destruction, i.e. decornification, is desirable, an excess of such zinc-containing compounds which also act as escharotics, e.g. zinc chloride, may be used. (Generally, concentrations of 35% (0.257 moles per 100 grams) or more zinc chloride will cause tissue destruction when topically applied.) Normally, use of equimolar concentrations of zinc chloride and the pharmacologically active agent will not involve the use of escharotic amounts of zinc chloride, however less than 35% zinc chloride should be considered an upper limit when no escharotic effect is desired. Less than an equimolar ratio of zinc-containing compound to pharmacologically active agent may be employed where it is not desired that all the medicament be absorbed into the skin or mucous membranes, e.g. in connection with mouthwash and douche preparations where attack on free-swimming organisms is also desirable.

Other ingredients may be added to the preparations, including coloring agents, stability-enhancing agents, antioxidants, and the like. Preferably these additives will not compete with the pharmacologically active agents for zinc; however when necessary, excess zinc-containing compounds may be used to compensate for the zinc complexing or chelating effect of such additives.

The pharmacologically active agents of this invention are those intended for topical application to achieve localized therapeutic or cosmetic effects. A partial list of suitable pharmacologically active agents includes steroids, antifungals, anti-unicellular microorganism agents, antiviral agents, antiparasitic agents, antineoplastic agents, anti-leprosy agents, antimetabolites, cell-regulatory agents, immuno-pharmacological agents, allergens, antihistaminic agents, anti-inflammatory agents, anesthetic agents, analgesic agents, counter-irritants, vitamins, nutrients, diagnostic agents, radiopaque agents, cryoprotective agents, perfumes, insect repellants, hair dyes, antiscarring agents, sun screens, melanin-stimulating agents, antiperspirants, antisecretory agents, depilatories, hair restorers, wrinkle-reducing agents, antidandruff agents, emollients, rubifacients, and cosmetic agents in general.

The mechanism by which the reservoir-inducing effect of this invention is produced is not known; however, it is preferred that the pharmacologically agents contain hydroxy, oxo, sulfhydryl, amine, carboxyl, or other anionic groups, or combinations thereof, in conformations which allow complexation and/or chelation by zinc ions.

Preferred pharmacologically active agents of this invention are:

1. Antineoplastic agents including NDGA (nordihydroguaiaretic acid), VP-16 (epipodophyllotoxin beta-D ethylidene glucopyranoside—etoposide), VM-26 (epipodophyllotoxin beta-D thenylidene glucopyranoside—teniposide), 4'demethyl epipodophyllotoxin, diethylstilbestrol, dithranol, cyclophosphamide, mitomycin, daunomycin, platinum cis-diamine-dichloride, adriamycin, allopurinol, 5-fluorouracil, and methotrexate.

2. Immunopharmacological agents which may be topically applied including polypeptide nanoparticles comprising interleuken or active fragments thereof, antibodies or active fragments thereof, interferons, and liposomes. Such delivery systems providing sustained release of pharmacologically active agents are effectively localized or held in place by zinc according to this invention.

3. Steroids, which are utilized for a wide range of therapeutic purposes including anti-inflammation, antipruritic, enhancement of moisture retention, etc., including: dexamethasone, hydrocortisone, hydrocortisone acetate, hydroxy hydrocortisone, hydrocortisone valerate, triamcinolone acetonide, triamcinolone hexacetonide, amcinonide, fluocinolone acetonide, fluocinonide, flurandrenolide, diflurrasone diacetate, betamethasone dipropionate, betamethasone, betamethasone benzoate, betamethasone valerate, halcinonide, desoximethasone, desonide, prednisolone, and clocortolone pivalate.

4. Antifungal agents which are used to treat fungus infections on the skin, hair, and nails, such as athlete's foot (*tinea pedis*), jock itch (*tinea cruris*), ringworm (*tinea corporis*), which can be caused by a number of fungi, particularly *Tricophyten rubrum, Trichophyten mentagrophytes,* and *Epidermophyton floccosum,* and *Microsporum canis.* These antifungal agents include haloprogin, iodochloro, miconazole nitrate, tolnaftate, thiabendazole, chloroxine, amphotericin, candicin, fungimycin, nystatin, chlordantoin, clotrimazole, ethonam nitrate, miconazole nitrate, pyrrolnitrin, fezatione, ticlatone, tolnaftate, triacetin, carbonic acid derivatives; dithiocarbamate, thiourea, thiocyantes; aromatic carboxylic acids and the amides thereof, benzoic acid, salicylic acid, salicylic acid amide and anilide; aromatic sulfides, polysulfides, and sulfoxides, 5,5-dichloro-2,2-dihydroxydiphenylsulfide; invert soaps, quaternary ammonia and phosphonium compounds, decamethylene-bis-(4-thio-pyridine-methyl-tosylate; quinoline derivatives, 8-hydroxyquinoline sulfate, halogenated quinolines, 7-iodo-8-hydroxyquinoline-5-sulfonic acid, 5-chloro-7-iodo-8-hydroxy-quinoline, 5-chloro-8-hydroxy-quinoline, 5,7-dichloro-8-hydroxyquinaldine, 5,7-diiodo-8-hydroxyquinoline, decamethylene-bis (4-aminoquinaldium chloride); benzothiazole derivates, (2-dimethylamino-6-(beta-diaminoethoxy)-benzothiazole dihydrochloride; imidazole derivatives, 1-(o-chloro-alpha-alpha-diphenyl-benzyl)-imidazole, 1-[o,p-dichloro-beta-(o,p-dichlorobenzyloxy)-phenethylimidazole]; benzimidazole derivatives, 2-phenylbenzimidazole, 2-furfurylbenzimidazole; thiadizine derivatives, 3,5-dibenzyltetrahydro-1,3,5-thiadizine-2-thione; furan derivatives, 5-nitro-2-furfuryl-3-chloropropionate; quinones, tetrachloro-p-benzoquinone, 1,4-naphthoquinone, phenanthraquinone; sulfonamides and sulfones; aromatic diamidines, 2-hydroxystilbamidine, and diamidinodiphenylamine.

Antifungal agents are also used to treat vaginal infections caused by *Candida albicans* and related yeasts; these agents include dioctyl sodium sulfosuccinate, haloprogin, miconazole nitrate, potassium sorbate, propionate compounds, such as calcium propionate and sodium propionate, and sodium lauryl sulfate.

5. Antibacterial agents, which are utilized for treating skin infections such as impetigo, ecthymus, folliculitis, boils, and acute pronychia, and for treating skin wounds and as a wound cleanser, and which may be used in this invention, including sulfonomides, penicillins, cephalosporins, penicillinase, lincomycins, vancomycins, tetracylines, chloramphenicols, and streptomycins; including within this group the following compounds: gramicidin, neomycin, polymyxin beta sulfate, tetracycline, benzethonium chloride, gentamicin sulfate, nitrofurazone, benzalkonium chloride, hexylresorcinol, chloroxylenol, cloflucarban, carbolic acid (phenol), triclocarban, and triclosan.

6. Antiviral agents, including those used to treat warts, such as glacial acetic acid, ascorbic acid, calcium pantothenate, lactic acid, salicylic acid, cantharidin, and podophyllin; and antiviral agents used to treat cold sores or herpes simplex such as acyclovir, benzalkonium chloride, alcohol, allantoin, anhydrous glycerin, benzocaine, camphor, carbamide peroxide, lanolin, menthol, petrolatum, and phenol; and antiviral agents including those used to treat herpes genitalis such as urea, idoxuridine, amantadine, methisazone, cytarabine, interferons, chloroform, ether, bacillus calmette-guerin, and levamisole.

7. Antiparasitic agents including antihelmintic agents (agents that destroy or expel intestinal worms) capable of penetrating the skin of the animal to be treated, e.g. benzimidazole compounds, tetramisole, levamisole, and isoquinoline compounds.

8. Pediculicides, for mites (or scabies) and lice, including lidane, pyrethrins, piperonyl butoxide, malathion, and crotamiton.

9. Acne treatment compounds including benzoyl peroxide, resorcinol, resorcinol monoacetate, sulfur, povidone-iodine, salicylic acid, phenol, fluocinolone acetonide, para-aminobenzoic acid, sodium thiosulfate, meclocyline sulfosalicylate, sodium sulfacetamide, tetracycline hydrochloride, aliphatic dicarboxylic acids, e.g. adipic and azelaic acids, and sulfurated lime.

10. Antipsoriasis agents including cytostatic agents, which retard skin-cell growth; keratolytic agents, which loosen and dissolve scales, tar preparations, whose mode of action is uncertain; hydrocortisone preparations, which reduce itching and inflammation; anti-itch preparations; and antimicrobials. These antipsoriasis agents include coal tar preparations, juniper tar, pine tar, allantoin, saponated cresol, menthol, mercury oleate, phenol preparations, resorcinol, salicylic acid, anthralin, and methotrexate.

11. Leprosy agents including 4-4'-diaminodiphenyl sulfone.

12. Anesthetic agents for pain and itching, inflamed skin, sunburn, insect bites, burns, wounds, hemorrhoids, poison ivy, poison oak, including: benzocaine, lidocaine, lidocaine hydrochloride, dibucaine, dibucaine hydrochloride, procaine, tetracaine, tetracaine hydrochloride, tronothane, dyclonine, dyclonine hydrochloride, pramoxine hydrochloride, benzyl alcohol, diperodon, butamben picrate, cyclomethycaine sulfate, and dimethisoquin hydrochloride.

13. Analgesic agents for pain and itching, inflamed skin, sunburn, insect bites, burns, wounds, hemorrhoids, poison ivy, poison oak, including: salicylic acid derivatives; N,N-dimethyl aspartic acid; N-N-dimethyl glutamic acid, trolamine salicylate, methyl salicylate; antipyrine, aspirin, and salicylamide.

14. Counter-irritants (agents applied locally to produce an inflammatory reaction with the object of distracting and relieving a deep seated inflammatory process) including methyl salicylate, camphor, menthol, eugenol, eucalyptol, thymol, allyl isothiocyanate (mustard oil), capsicum preparations, histamine dihydrochloride, methyl nicotinate, and turpentine oil.

15. Antihistamines which are used principally against itching, but are also mildly anesthetic, including diphenhydramine hydrochloride, phenyltoloxamine dihydrogen citrate, pyrilamine maleate, tripelennamine hydrochloride.

16. Diagnostic agents including allergenic extracts for diagnosis and immunotherapy of specific allergy offenders from the following categories: pollens, foods, dusts, epidermals, insects and stinging insects, fungi, molds, yeasts; tests for sensitivity to therapeutic penicillin (benzyl-penicilloyl-polylsine); tests for sensitivity to tetanus antigens, diphtheria antigens, streptococcus antigens, tuberculin, Candida antigens, Trichophyton antigens, and Proteus antigens.

17. Vitamins and nutrients for skin, hair, and scalp conditions, including anti-scarring agents, vitamins $B_3$, $B_5$, $B_6$, A, D, and E.

18. Cosmetic agents and perfumes including compositions to reduce the appearance of wrinkles such as water soluble elastin and pregnenolone; skin depigmenting agents and bleaches, including hydroquinone and monobenzone.

19. Sunscreens including: dioxybenzone, oxybenzone, padimate O, padimate A, aminobenzoic acid, cinoxate, diethanolamine p-methoxycinnamate, ethyl 4-[bis(hydroxypropyl)]aminobenzoate, ethylhexyl salicylate, glyceryl aminobenzoate, homosalate, the combination of lawsone and dihydroxyacetone, red petrolatum, and sulisobenzone.

The foregoing are simply examples of pharmacologically active agents including therapeutic and cosmetic agents which may be used with enhanced effectiveness for their known properties in accordance with this invention.

In addition to the reservoir effect produced by zinc ions in skin and mucous membranes, a direct potentiating effect has been observed when pharmaceutical preparations containing zinc ions and pharmacologically active agents are injected directly into diseased tissues, particularly solid tumors. The mechanism for this potentiating effect is not known; however, it may be caused by a reservoir-inducing effect directly on the tissues involved.

Dosage forms for topical application may include lotions, ointments, creams, gels, suppositories, nasal solutions, mouthwashes, sprays, aerosols and the like. Typical carriers which make up the foregoing dosage forms include water, acetone, isopropyl alcohol, stearyl alcohol, freons, ethyl alcohol, polyvinyl pyrrolidone, propylene glycol, polyethlyene glycol, fragrances, gel-producing materials, mineral oil, stearic acid, spermaceti, sorbitan, monoleate, polysorbates, "Tweens," sorbitol, methyl cellulose, etc.

The amount of the composition, and thus of the pharmacologically active agent therein to be administered, will obviously be an effective amount for the desired result expected therefrom. This, of course, will be ascertained by the practitioner utilizing his ordinary skill. Due to enhanced activity which is achieved, the dosage of agent may often be decreased from that generally applicable. In accordance with usual prudent formulating practices, a dosage near the lower useful range of the particular agent may be employed initially and the dosage increased as indicated from the observed response.

Preferred compositions are illustrated in the following examples:

EXAMPLE 1

Antineoplastic Preparation

Two compositions utilizing zinc chloride, nordihydroguaiaretic acid (NDGA), acid (EDTA), butylated hydroxytolulene (BHT), stearyl alcohol, purified water, polyethylene gylcol having an average molecular weight of 400 (PEGO 400), and polyethylene glycol having an average molecular weight of 3350 (PEGO 3350) were prepared in the following manner: the purified water was placed in a clean glass container of suitable capacity; the water was heated to about 80°–90° C. with stirring; and zinc chloride was added to the heated water, continuing the stirring until the zinc chloride dissolved. The ethylenediaminetetraacetic acid was next slowly added with mixing until dissolved. In a separate glass container of suitable size, the polyethylene glycol 400 was heated to about 80°–90° C. with stirring; the NDGA was added thereto; then the BHT; and this mixture was added to the zinc chlorideethylenediaminetetraacetic acid solution with stirring. The entire mixture was then cooled to about room temperature and passed through a number 3 roller mill until smooth. The polyethylene glycol 3350 was then heated to about 80°–90° C. in a suitable container and the milled ingredients added thereto with mixing.

The final compositions in wt/wt % were as follows:

TABLE 1

| Composition | Compound A | Compound B |
|---|---|---|
| zinc chloride | 29.8 | 10.0 |
| NDGA | 4.6 | 4.6 |
| EDTA | 14.7 | 4.93 |
| BHT | 1.1 | 1.1 |
| stearyl alcohol | 0.5 | 0.5 |
| H$_2$O | 18.3 | 18.3 |
| PEGO 400 | 26.4 | 26.4 |
| PEGO 3350 | 4.5 | 4.5 |

EXAMPLE 2

Reservoir Effect

This study was designed to provide basic pharmacokinetic data on the disposition of Carbon 14 ($^{14}$C) labelled nordihydroguaiaretic acid (NDGA) applied dermally in modified compounds A and B described in Example 1. In addition, the distribution of zinc was measured for the dermally applied Compound A.

The $^{14}$C-NDGA compound exhibited a specific radioactivity of 20.2 Ci/mole (66.9 micro Ci/mg) and a purity of 96.9% by mass spectrometry and by radioautography of thin-layer chromatography plates developed in benzene:isopropanol:acetic acid:water (25:5:2:10).

Subsequently, 25.1 mg of the $^{14}$C-NDGA-Compound (66.9 micro Ci/mg) were mixed with 12.35 g of Compound A. Analyses of triplicate samples of the final mixture for $^{14}$C by counting and for NDGA by high-pressure liquid chromatography (HPLC) demonstrated homogeneity, with a content of 51 micro g of $^{14}$C-NDGA compound/mg of Compound A. The specific radioactivity of the NDGA was $3.00 \times 10^3$ micro Ci/micro g.

Similarly, 26.3 mg of the original $^{14}$C-NDGA compound (66.9 micro Ci/mg) were mixed with 12.55 g of Compound A devoid of Z and EDTA to obtain a mixture for the study of the dermal penetration of NDGA from Compound A devoid of Z and EA. Analyses of triplicate samples of the modified Compound A showed the final mixture to be homogeneous with regard to $^{14}$C and NDGA; it contained 53 micro g of $^{14}$C-NDGA compound/mg of vehicle. The specific radioactivity of the diluted NDGA was $3.41 \times 10^{-3}$ micro Ci/micro g.

The compounds were dermally applied to young adult Sprague-Dawley rats by the following protocol: under ether anesthesia, the back skin of the rat was prepared by removing the hair from a 5×5-cm area with a clipper and, the residual hair stubble was removed with a wax depilatory. Then the skin was stripped repeatedly (5×) with adhesive tape until the stratum corneum was removed. Then 0.5 gm of the formulation was weighed on a 5×5-cm sheet of polypropylene, which was applied to the prepared skin. It was secured in place by hypoallergenic tape. Finally, the bandage was overwrapped with bandage tape. After treatment, the rats were caged individually in metabolism cages, which allowed free access to food and water and provided for separate collection of urine and feces.

The testing of Compound A with $^{14}$C-NDGA was performed in 15 male Sprague-Dawley rats (mean weight 339±16 g). They received an average of 0.520 (±0.032) g of Compound A containing $^{14}$C-NDGA. The mean dose of $^{14}$C-NDGA was 78.5 (±7.0) mg/kg of body weight. The rats were housed individually in metabolism cages providing for free access to food and water and for the separate collection of urine and feces. Groups of 3 rats were sacrificed at 4, 24, 48, 72, and 96 hr and excreta were collected from each rat during 24-hr periods. In addition to the usual collection of tissues, the skin site of application was excised after wiping the site with water-moistened tissue. The wipes were added to the wrappings, which were immersed in a small container of acetone.

The testing of Compound A devoid of Zn and EDTA was performed on 15 male Sprague-Dawley rats (mean weight 241±7 g). They received an average of 0.390 (±0.019) g of Zn-free C205 containing $^{14}$C-NDGA. The average dose of $^{14}$C-NDGA was 83.2 mg/kg of body weight. Groups of three rats were bled terminally and tissues were taken at 4, 24, 48, 72, and 96 hr after dosing. At each sacrifice time, those three rats scheduled to be sacrificed next were also bled nonterminally from the orbital sinus. The wrappings and wipes of the skin site were taken at the time of sacrifice and added to acetone as described above.

The results of the study are given in Table 2A for Compound A containing $^{14}$C-NDGA. and Table 2B for Zn-Free Compound A containing $^{14}$C-NDGA. The results of analysis for tissue distribution of zinc as a percent of dose in rats receiving Compound A containing $^{14}$C-NDGA are given in Table 2C.

TABLE 2A

Tissue Distribution of $^{14}C$ as a Percent of Dose in Rats Receiving Compound A Containing $^{14}C$—NDGA, Dermally

| | Mean (± S.D.)[a] Percent of the Dose of $^{14}C$ Found at Hours | | | | |
|---|---|---|---|---|---|
| Tissue | 4 | 24 | 48 | 72 | 96 |
| Organs (%) | 4.62 (±2.27) | 7.55 (±1.85) | 10.29 (±8.8) | 10.43 (±6.94) | 13.45 (±3.45) |
| Skinsite (%) | 20.8 (±8.4) | 19.6 (±5.2) | 11.1 (±1.4) | 8.58 (±5.41) | 7.01 (±2.28) |

[a]N = 3

TABLE 2B

Tissue Distribution of $^{14}C$ as a Percent of Dose in Rats Receiving Zn-Free Compound A Containing $^{14}C$—NDGA, Dermally

| | Mean (±S.D.)[a] Percent of the Dose of $^{14}C$ Found at Hours | | | | |
|---|---|---|---|---|---|
| Tissue | 4 | 24 | 48 | 72 | 96 |
| Organs % | 10.28 (±6.12) | 11.08 (±9.65) | 10.47 (±10.33) | 5.41 (±4.21) | 8.03 (±1.48) |
| Skinsite (%) | 4.15 (±0.76) | 12.20 (±5.9) | 7.86 (±3.75) | 4.72 (±3.18) | 1.43 (±0.55) |

[a]N = 3

TABLE 2C

Tissue Distribution of Zn as a Percent of Dose in Rats Receiving Compound A, Dermally

| | Mean Percent of the Dose of Zn found at Hours | | | | |
|---|---|---|---|---|---|
| Tissue | 4 | 24 | 48 | 72 | 96 |
| Organs (%) | 3.28 | 6.54 | 6.79 | 11.47 | 12.69 |
| Skinsite (%) | 10.5 | 11.8 | 9.58 | 6.46 | 4.99 |

[a]N = 3

The study was continued for testing Compound B with $^{14}C$-NDGA; Zn- and EDTA-free Compound B; and modified Compound B with no BHT and 0.10 EDTA. The following Table 2D lists the compositions of the compounds and the amounts of materials used for preparing the compounds containing $^{14}C$-NDGA. These compounds were analyzed for $^{14}C$ by scintillation counting and for NDGA by liquid chromatography.

TABLE 2D

| | Composition (%) | | |
|---|---|---|---|
| Constituent | Compound B Formulation | Zn-Free Compound B Formulation | Modified Compound B Formulation |
| Compound Zn | 10.00 | 0.00 | 10.00 |
| Compound EDTA | 4.93 | 0.00 | 0.10 |
| Compound NDGA | 4.60 | 4.60 | 4.60 |
| Compound BHT | 1.10 | 1.10 | 0.00 |
| Water, purified | 18.32 | 18.32 | 19.42 |
| PEG 400 | 2.60 | 14.50 | 14.19 |
| PEG 8000 | 53.45 | 49.39 | 46.69 |
| Stearyl Alcohol | 5.00 | 12.09 | 5.00 |
| | 100% | 100% | 100% |
| Compounds containing $^{14}C$—NDGA: | | | |
| mg of $^{14}C$—NDGA | 25.75 | 25.40 | 25.20 |
| g of Formulation | 12.55 | 12.55 | 12.75 |
| % NDGA in final mixture | 4.80 | 4.79 | 4.78 |

The mean rat body weights, average doses of the formulations, and mean doses of $^{14}C$-NDGA in mg/kg of body weight for the three current protocols were: 297±15 g (standard deviation), 512±28 mg, and 82.7±2.0 mg/kg for Compound B; 325±12 g, 570±26 mg, and 84.0±1.4 mg/kg for Zn-free Compound B; and 328±27 g, 575±45 mg, and 84.2±2.8 mg/kg for modified Compound B. Fifteen rats were used for each study and groups of three rats were sacrificed at 4, 24, 48, 48, 72 and 96 hr after dosing. At each time, blood, liver, skin site, intestines and contents, carcass, and combined wrappings and wipes were collected. Also, from the groups sacrificed at 24, 48, 72, and 96 hr urine, feces, and cage washings were collected.

The results of the study are given in Table 2E for Compound B; Table 2F for Zn-free Compound B; and Table 2G for modified Compound B.

TABLE 2E

Tissue Distribution of $^{14}C$ as a Percent of Dose in Rats Receiving Compound B Containing $^{14}C$—NDGA, Dermally

| | Mean (±S.D.)[a] Percent of the Dose of $^{14}C$ Found at Hours | | | | |
|---|---|---|---|---|---|
| Tissue | 4 | 24 | 48 | 72 | 96 |
| Organs (%) | 1.92 (±1.34) | 4.41 (±1.44) | 4.31 (±2.5) | 3.38 (±0.52) | 1.87 (±1.1) |
| Skinsite (%) | 16.3 (±9.2) | 11.9 (±6.1) | 8.92 (±4.10) | 6.55 (±1.76) | 5.11 (±3.01) |

[a]N = 3

TABLE 2F

Tissue Distribution of $^{14}C$ as a Percent of Dose in Rats Receiving Zn-Free Compound B Containing $^{14}C$—NDGA, Dermally

| | Mean (±S.D.)[a] Percent of the Dose of $^{14}C$ Found at Hours | | | | |
|---|---|---|---|---|---|
| Tissue | 4 | 24 | 48 | 72 | 96 |
| Organs (%) | 1.16 (±0.92) | 2.29 (±2.26) | 2.38 (±1.73) | 7.39 (±10.05) | 7.73 (±10.9) |
| Skinsite (%) | 2.21 (±1.44) | 4.45 (±4.36) | 6.07 (±2.90) | 18.6 (±6.3) | 12.0 (±4.99) |

[a]N = 3

TABLE 2G

Tissue Distribution of $^{14}C$ as a Percent of Dose in Rats Receiving Modified Compound B Containing $^{14}C$—NDGA, Dermally

| | Mean (±S.D.)[a] Percent of the Dose of $^{14}C$ Found at Hours | | | | |
|---|---|---|---|---|---|
| Tissue | 4 | 24 | 48 | 72 | 96 |
| Organs (%) | 4.35 (±3.06) | 1.65 (±0.68) | 4.41 (±3.57) | 2.54 (±2.05) | 0.97 (±0.19) |
| Skinsite (%) | 14.4 (±7.1) | 23.0 (±5.5) | 17.1 (±4.7) | 16.3 (±0.6) | 17.7 (±6.2) |

[a]N = 3

The above results show that the addition of the water-soluble zinc-containing compound causes the organic molecule to more quickly absorb into the skin in larger quantities, and to be retained in the skin longer than when the zinc-containing compound is not present.

EXAMPLE 3

Antineoplastic Enhancement

For the organic compounds listed, in the case of those having two or more benzene rings, .0145 moles per 100 cc's was used, and for those having one or no benzene rings, 0.029 moles per 100 cc's was used. The organic compound was measured into a clean vial and PEGO 400 was added with mixing until dissolved.

For the test compounds containing zinc chloride, zinc chloride was first dissolved in the PEGO 400 to prepare a stock solution containing 0.69% zinc chloride, and this solution was added with mixing to the vials containing the organic compounds being tested.

These compounds were tested with and without zinc chloride for their effectiveness as antitumor agents against xenografts of human breast adenocarcinoma, MX-1, grown in athymic (nude) mice of Balb/c background by intratumor injection according to the following protocol: each animal was inoculated intradermally on the dorsum near the nape of the neck with 0.05 ml of an MX-1 tumor homogenate. Tumor weights, in milligrams, were calculated from a measurement of the length, width and height in millimeters of the tumors using the formula $(L \times W \times H)/2$. The animals were randomized in groups to ensure representation of smaller and larger tumors. The tumors were treated by intratumor injection with 0.01 ml of each test composition. Each composition was tested utilizing five animals. The animals were treated only once. Results are set forth in Table 3.

TABLE 3

| Organic Compound Compound Known Anti-Cancer Agent | Tumor Free 60 Days | Premature Death | Tumor at Death | Tumor Recurrence |
|---|---|---|---|---|
| VP-16 (no Zn) | 2 | 2 | 3 | 0 |
| VP-16 + Zn | 5 | 0 | 0 | 0 |
| *1/5 VP-16 + Zn | 3 | 0 | 2 | 2 |
| VM-26 (no Zn) | 0 | 0 | 5 | 0 |
| VM-26 + Zn | 5 | 0 | 0 | 0 |
| *1/5 VM-26 + Zn | 5 | 0 | 0 | 0 |
| 4'-demethylepipodophyllotoxin (no Zn) | 1 | 0 | 4 | 3 |
| 4'-demethylepipodophyllotoxin + Zn | 5 | 0 | 0 | 0 |
| diethylstilbestrol (no Zn) | 0 | 2 | 5 | 0 |
| diethylstilbestrol + Zn | 3 | 0 | 2 | 1 |
| dithranol (no Zn) | 1 | 0 | 4 | 0 |
| dithranol + Zn | 4 | 0 | 1 | 1 |
| cyclophosphamide (no Zn) | 0 | 0 | 5 | 0 |
| cyclophosphamide + Zn | 3 | 2 | 0 | 0 |
| mitomycin (no Zn) | 1 | 4 | 2 | 0 |
| mitomycin + Zn | 5 | 0 | 0 | 0 |
| daunomycin (no Zn) | 3 | 2 | 5 | 3 |
| daunomycin + Zn | 5 | 0 | 0 | 0 |
| platinum cis-diaminedichloride (no Zn) | 1 | 0 | 4 | 0 |
| platinum cis-diaminedichloride + Zn | 5 | 0 | 0 | 0 |
| adriamycin (no Zn) | 0 | 1 | 2 | 4 |
| *1/10 adriamycin (no Zn) | 2 | 1 | 2 | 2 |
| adriamycin + Zn | 4 | 0 | 1 | 1 |
| *1/10 adriamycin + Zn | 1 | 3 | 1 | 1 |
| allopurinol (no Zn)** | 0 | — | 5 | — |
| *5/2 allopurinol (no Zn) | 0 | 0 | 5 | 0 |
| allopurinol + Zn | 1 | 0 | 4 | 4 |
| *5/2 allopurinol + Zn | 1 | 0 | 4 | 4 |

*Dosage level decreased or increased as indicated.
**All sacrificed on day 25.

These results show the reduced toxicity and enhanced antineoplastic effectiveness achieved by the addition of zinc ions.

EXAMPLE 4

Antineoplastic Potentiation

Compositions and organic compounds not previously known as antineoplastic agents were prepared with and without zinc chloride according to the procedure of Example 3 and tested for their ability to eradicate tumors following the protocol described in Example 3. Results are set forth in Table 4.

TABLE 4

| Organic Compound | Tumor Free 60 Days | Premature Death | Tumor at Death | Tumor Recurrence |
|---|---|---|---|---|
| 3-tertbutylphenol (no Zn) | 1 | 3 | 1 | 0 |
| 3-tertbutylphenol + Zn | 5 | 0 | 0 | 0 |
| 4-tertbutylphenol (no Zn) | 5 | 0 | 0 | 0 |
| 4-terbutylphenol + Zn | 5 | 0 | 0 | 0 |
| p-hydroxycinnamic acid (no Zn) | 1 | 0 | 4 | 0 |
| p-hydroxycinnamic acid + Zn | 4 | 1 | 0 | 0 |
| norisoguaiacin (no Zn) | 2 | 1 | 1 | 0 |
| norisoguaiacin + Zn | 5 | 0 | 0 | 0 |
| dl-NDGA (no Zn) | 4 | 0 | 1 | 0 |
| dl-NDGA + Zn | 5 | 0 | 0 | 0 |
| azelaic acid (no Zn) | 1 | 0 | 4 | 0 |
| azelaic acid + Zn | 5 | 0 | 0 | 0 |
| 1-(3,4-diacetoxyphenyl)-4-phenyl-buta-1,3-diene (no Zn) | 1 | 0 | 4 | 0 |
| 1-(3,4-diacetoxyphenyl)-4-phenyl-buta-1,3-diene + Zn | 3 | 0 | 2 | 2 |
| 1,4-bis(3,4-dihydroxyphenethyl)-benzene (no Zn) | 2 | 0 | 3 | 3 |
| 1,4-bis(3,4-dihydroxyphenethyl)-benzene + Zn | 2 | 0 | 3 | 3 |

These results show that the antineoplastic activity of drugs can be increased to worthwhile levels while at the same time reducing toxicity utilizing zinc ions.

EXAMPLES 5-10

Enhancement of Topical Antineoplastic Agents

In Examples 5-10, wherein reference is made to the testing of mixtures for antitumor activity against B-16 melanoma and Sarcoma-180 solid tumor growth in mice, the following procedures were utilized. To the extent that a particular example modified the procedure, such modification will be indicated in the particular example.

Both types of tumors were grown intradermally or subcutaneously in the mice. The B-16 melanoma was grown in $BDF_1$ mice and the S-180 tumor was grown in ICR mice. Each mouse was injected intradermally with about 0.01 ml of a saline suspension containing about $1 \times 10^6$ cells of the tumor cells per 0.01 ml into a preshaven area on the back of the neck of the mouse. The tumors were allowed to grow until they had an approximate size of about 25-100 mg, calculated by the length of the tumor multiplied by the width and height of the tumor measured in millimeters and dividing the product by two. On the first day of treatment, the animals with tumor sizes outside of the size range were culled and the remaining animals were randomly divided into control and test groups. When the tumors had reached the appropriate size, usually at about day six, the tumors were punctured uniformly and then treated with either a test compound or a control by topical application to the surface of the tumor. Generally, two topical applications were made 24 hours apart. The materials were applied to obtain from about a 1 to about 2 mm coating over the surface of the tumor. The animals were thereafter observed and their weights and the size of their tumors were periodically measured.

The results of each of the experiments include the following:
  (a) the starting number starting number (n) of animals within a treatment group of an experiment;
  (b) the average tumor size in milligrams of the animals treated with the mixture and the average tumor size of the control animals;
  (c) the ratio multiplied by 100 of the average size of the tumors of the treated animals to that of the control animals (T/C), wherein T=average size of treated mice and C=average tumor size of control mice;
  (d) the percentage of both treated and control animals clear of tumor; and
  (e) the percentage of animals of the original number surviving.

The later three measurements for a particular experiment were all taken at the same time and range generally from 21 to about 33 days after tumor innoculation. A T/C value of 42 or less is indicative of activity. In all of the following tables for Examples 5-10, the control results are given in parenthesis ( ).

EXAMPLE 5

Two formulations of meso-NDGA were prepared in a PEGO base. Their compositions are as set forth in Table 5.

TABLE 5

| Mixture | NDGA (meso) | H$_2$O | EtOH | PEGO 3350 |
|---|---|---|---|---|
| 1 | 3.6 | 24.3 | 48.5 | 23.4 |
| 2 | 6.9 | 0 | 0 | 93.1 |

Mixture No. 1 was prepared by dissolving the NDGA in absolute ethanol by warming and stirring; thereafter, the water was added slowly to the NDGA solution. The mixture was heated to evaporate sufficient solvent to obtain a mixture of about 130% of the weight of the NDGA, and was then incorporated into the PEGO base. Mixture No. 2 was made by simply dissolving the NDGA in the PEGO base with warming and stirring.

EXAMPLE 6

The NDGA formulations of Example 5 were tested for potential antitumor activity against B-16 melanoma grown in mice. The procedure utilized was that previously described. The results are given below in Table 6.

TABLE 6

| n | T/C[1] | Tumor Size (Control) | % Clear (Control) | % Survival (Control) |
|---|---|---|---|---|
| 9 | 87 | 954 ± 698 | 0 | 33 |
|   |   | (1091 ± 547) | (0) | (80) |
| 9 | 114 | 748 ± 621 | 0 | 77 |
|   |   | (645 ± 335) | (0) | (77) |
| 10* | 24 | 138 ± 99 | 20 | 100 |
|   |   | 575 ± 270 | (0) | (60) |

[1]T/C ratio was calculated between days 21-24.
*Animal treated once via a 0.05 ml. intratumor injection on day 6 after tumor inoculation

EXAMPLE 7

Several formulations of zinc chloride in a PEGO base were prepared by first dissolving the zinc chloride in water and then mixing the zinc chloride solution into the PEGO base. The formulations had approximately the following weight/weight percent compositions as set forth in Table 7.

TABLE 7

| Mixture | ZnCl$_2$ | H$_2$O | PEGO |
|---|---|---|---|
| 3 | 41.9 | 11.6 | 46.5 |
| 4 | 30 | 16 | 53.8 |
| 5 | 14.6 | 4.1 | 81.3 |
| 6 | 28.6 | 7.9 | 63.5 |
| 7 | 46.1 | 13.8 | 40 |
| 8 | 15 | 8 | 77 |
| 9 | 13.8 | 9.2 | 77 |
| 10 | 5.5 | 3.7 | 90.8 |

EXAMPLE 8

Mixtures of Example 7 were tested for potential antitumor activity against B-16 melanoma and S-180 solid tumor grown in mice in accordance with the procedures previously described. The results are given in Table 8.

EXAMPLE 8

S-180

| Mixture | n | T/C[1] | Tumor Size (Control) | % Clear (Control) | % Survival (Control) |
|---|---|---|---|---|---|
| 3 | 8 | 51 | 559 ± 476 | 25 | 100 |
|   |   |   | (1095 ± 360) | (10) | (100) |
| 3 | 10 | 40 | 366 ± 345 | 11 | 90 |
|   |   |   | (934 ± 656) | (10) | (100) |
| 6 | 8 | 48 | 524 ± 462 | 12 | 100 |
|   |   |   | (1095 ± 360) | (10) | (100) |
| 6 | 10 | 115 | 1074 ± 687 | 10 | 100 |
|   |   |   | (934 ± 656) | (10) | (100) |
| 7 | 5 | 0 | 0 | 100 | 80 |
|   |   |   | (752 ± 511) | (0) | (100) |
| 7 | 10 | 0 | 0 | 100 | 90 |
|   |   |   | (550 ± 184) | (0) | (100) |
| 7 | 10 | 0 | 0 | 100 | 100 |
|   |   |   | (997 ± 421) | (0) | — |
| 10 | 8 | 74 | 815 ± 472 | 0 | 87 |
|   |   |   | (1095 ± 360) | (10) | (100) |

[1]T/C ratio calculated between days 20-23.

B-16

| Mixture | n | T/C[1] | Tumor Size (Control) | % Clear (Control) | % Survival (Control) |
|---|---|---|---|---|---|
| 3 | 10 | 6 | 162 ± 253 | 60 | 100 |
|   |   |   | (2505 ± 1844) | (0) | (100) |
| 4 | 10 | 16 | 106 ± 114 | 30 | 100 |
|   |   |   | (644 ± 342) | (0) | (70) |
| 5 | 10 | 47 | 1191 ± 764 | 22 | 90 |
|   |   |   | (2505 ± 1844) | (0) | (100) |
| 6 | 10 | 4 | 94 ± 217 | 80 | 100 |
|   |   |   | (2502 ± 1844) | (0) | (100) |
| 7 | 9 | 15 | 169 ± 216 | 37 | 88 |
|   |   |   | (1091 ± 547) | (0) | (80) |
| 7 | 9 | 0 | 0 | 100 | 88 |
|   |   |   | (654 ± 335) | (0) | (77) |
| 7 | 10 | 2 | 31 ± 100 | 90 | 100 |
|   |   |   | (1805 ± 968) | (0) | (80) |
| 8 | 10 | 43 | 277 ± 209 | 10 | 40 |
|   |   |   | (644 ± 342) | (0) | (70) |
| 9 | 10 | 1.0 | 25 ± 63 | 80 | 90 |
|   |   |   | (1733 ± 2254) | (70) | (80) |

[1]T/C ratio calculated between days 21 and 25.

EXAMPLE 9

Mixtures of zinc chloride, EDTA and NDGA were prepared and formulated in a PEGO base. The mixtures were prepared by dissolving the NDGA and EDTA in a portion of the PEGO base by warming and stirring until dissolved. The zinc chloride was dissolved in water and warmed. The warm zinc chloride solution was added to the warm PEGO containing the NDGA and EDTA and stirred until cooled to room temperature. The composition of the mixtures is given in approximate weight/weight percentage as set forth in Table 9.

TABLE 9

| Mixture | ZnCl$_2$ | NDGA | EDTA | H$_2$O | PEGO |
|---|---|---|---|---|---|
| 11 | 27.5 | 6.9 | 14.7 | 18.3 | 32.6 |
| 12 | 28 | 6.8[1] | 14.7 | 18.2 | 32.9 |

EXAMPLE 10

The mixtures of Example 9 were tested for their potential antitumor activities against B-16 melanomas grown in mice in accordance with the procedure previously described. The results are given in Table 10.

TABLE 10

| | | | B-16 | | |
|---|---|---|---|---|---|
| Mixture | n | T/C[1] | Tumor Size (Control) | % Clear (Control) | % Survival (Control) |
| 11 | 10 | 8 | 51 ± 118 (711 ± 286) | 70 (0) | 100 (100) |
| 12 | 10 | 0 | 0 (711 ± 286) | 60 (0) | 100 (100) |

[1] T/C ratio calculated at day 24 except for Mixture 11 which was calculated at day 21.

The foregoing Examples 5–10 show the potentiating effect of zinc chloride on antineoplastic agents topically applied, showing improvement over the antineoplastic activity of zinc chloride alone, and comparable amounts of NDGA even when the NDGA is injected into the tumor.

EXAMPLE 11

Appropriate human and animal models are chosen for the disease conditions treated by the following compounds as herinabove described, and the compounds tested to determine effective and toxic dosages with and without the addition of equimolar amounts of zinc chloride, zinc iodide, zinc bromide, zinc sulfate, zinc nitrate, zinc stearate, and zinc acetate. From the results the Therapeutic Index, equivalent to ratio of toxic to effective dosage is calculated, and this Index for the compounds with and without zinc additives compared to show an increase in Therapeutic Index for compounds containing zinc additives as compared to compounds without such additives: NDGA (nordihydroguaiaretic acid), VP-16 (epipodophyllotoxin beta-D ethylidene glucopyranoside—etoposide), VM-26 (epipodophyllotoxin beta-D thenylidene glucopyranoside—teniposide), 4'demethyl epipodophyllotoxin, diethylstilbestrol, dithranol, cyclophosphamide, mitomycin, daunomycin, platinum cis-diamine-dichloride, adriamycin, allopurinol, 5-fluorouracil, methotrexate, dexamethasone, hydrocortisone, hydrocortisone acetate, hydroxy hydrocortisone, hydrocortisone valerate, triamcinolone acetonide, triamcinolone hexacetonide, amcinonide, fluocinolone acetonide, fluocinonide, flurandrenolide, difluorasone diacetate, betamethasone dipropionate, betamethasone, betamethasone benzoate, betamethasone valerate, halcinonide, desoximethasone, desonide, prednisolone, clocortolone pivalate, haloprogin, iodochloro, miconazole nitrate, tolnaftate, thiabendazole, chloroxine, amphotericin, candicin, fungimycin, nystatin, chlordantoin, clotrimazole, ethonam nitrate, miconazole nitrate, pyrrolnitrin, fezatione, ticlatone, tolnaftate, triacetin, dithiocarbamate, thiourea, thiocyantes; aromatic carboxylic acids and the amides thereof, benzoic acid, salicylic acid, salicylic acid amide and anilide; aromatic sulfides, polysulfides, and sulfoxides, 5,5-dichloro-2,2-dihydroxydiphenylsulfide; quaternary ammonia and phosphonium compounds, decamethylene-bis-(4-thiopyridine-methyl-tosylate; 8-hydroxyquinoline sulfate, halogenated quinolines, 7-iodo-8-hydroxy-quinoline-5-sulfonic acid, 5-chloro-7-iodo-8-hydroxy-quinoline, 5-chloro-8-hydroxy-quinoline, 5,7-dichloro-8-hydroxyquinaldine, 5,7-diiodo-8-hydroxyquinoline, decamethylenebis (4-amino-quinaldium chloride); (2-dimethylamino-6-(beta-diaminoethoxy)-benzothiazole dihydrochloride; 1-(o-chloro-alpha-alpha-diphenyl-benzyl)-imidazole, 1-[o,p-dichloro-beta-(o,p-dichlorobenzyloxy)-phene-thylimidazole]; 2-phenylbenzimidazole, 2-furfurylbenzimidazole; 3,5-dibenzyltetrahydro-1,3,5-thiadizine-2-thione; 5-nitro-2-furfuryl-3-chloropropionate; quinones, tetrachloro-p-benzoquinone, 1,4-naphthoquinone, phenanthraquinone; sulfonamide sulfones; aromatic diamidines, 2-hydroxystilbamidine, diamidinodiphenylamine, dioctyl sodium sulfosuccinate, miconazole nitrate, potassium sorbate, calcium propionate and sodium propionate, sodium lauryl sulfate, penicillin, cephalosporin, penicillinase, lincomycins, vancomycin, tetracyline, chloramphenicol, streptomycin, gramicidin, neomycin, polymyxin beta sulfate, tetracycline, benzethonium chloride, gentamicin sulfate, nitrofurazone, benzalkonium chloride, hexylresorcinol, chloroxylenol, cloflucarban, carbolic acid (phenol), triclocarban, triclosan, glacial acetic acid, ascorbic acid, calcium pantothenate, lactic acid, salicylic acid, cantharidin, podophyllin, acyclovir, benzalkonium chloride, alcohol, allantoin, anhydrous glycerin, benzocaine, camphor, carbamide peroxide, lanolin, menthol, petrolatum, phenol, idoxuridine, amantadine, methisazone, cytarabine, interferon, chloroform, ether, bacillus calmette-guerin, levamisole, benzimidazole, tetramisole, levamisole, isoquinoline, lidane, pyrethrin, piperonyl butoxide, malathion, crotamiton, benzoyl peroxide, resorcinol monoacetate, sulfur, povidone-iodine, phenol, fluocinolone acetonide, para-aminobenzoic acid, sodium thiosulfate, meclocyline sulfosalicylate, sodium sulfacetamide, tetracycline hydrochloride, 6-2 carbon aliphatic dicarboxylic acids, sulfurated lime, coal tar, juniper tar, pine tar, allantoin, saponated cresol, menthol, mercury oleate, phenol, methotrexate 4-4'-diaminodiphenyl sulfone, benzocaine, lidocaine, lidocaine hydrochloride, dibucaine, dibucaine hydrochloride, procaine, tetracaine, tetracaine hydrochloride, tronothane, dyclonine, dyclonine hydrochloride, pramoxine hydrochloride, benzyl alcohol, diperodon, butamben picrate, cyclomethycaine sulfate, dimethisoquin hydrochloride, N,N-dimethyl aspartic acid; N-N-dimethyl glutamic acid, trolamine salicylate, methyl salicylate; antipyrine, salicylamide, camphor, eugenol, eucalyptol, thymol, allyl isothiocyanate (mustard oil), capsicum preparations, histamine dihydrochloride, methyl nicotinate, turpentine oil, diphenhydramine hydrochloride, phenyltoloxamine dihydrogen citrate, pyrilamine maleate, tripelennamine hydrochloride, tetanus antigen, diphtheria antigen, streptococcus antigen, tuberculin, Candida antigen, Trichophyton antigen, Proteus antigen, vitamins B$_3$, B$_5$, B$_6$, A, D, and E, elastin, pregnenolone, hydroquinone, monobenzone, dioxybenzone, oxybenzone, padimate O, padimate A, aminobenzoic acid, cinoxate, diethanolamine p-methoxycinnamate, ethyl 4-[bis(hydroxypropyl)]aminobenzoate, ethylhexyl salicylate, glyceryl aminobenzoate, homosalate, lawsone, dihydroxyacetone, red petrolatum, and sulisobenzone.

The foregoing examples are illustrative of the methods and compositions of this invention and are not intended to be limiting. The present invention is believed to be a pioneering invention in the area of drug potentiation, and as such embraces many equivalents not specifically described herein.

What is claimed is:

1. A method of enhancing penetration of the skin and mucous membrane by a pharmacologically active agent and retention of said pharmacologically active agent therein comprising the application to the skin of a composition comprising said pharmacologically active agent and an effective penetrating and retaining amount of a water-soluble zinc-containing compound which acts to reduce the transdermal flux through the skin and mucous membrane of the pharmacologically active agent.

2. The method of Claim 1 wherein said pharmacologically active agent is selected from the group consisting of: steroids, antiparasitic agents, antileprosy agents, antimetabolites, cell-regulatory agents, immuno-pharmacological agents, allergens, antihistaminic agents, anti-inflammatory agents, anesthetic agents, counter-irritants, skin vitamins and nutrients, diagnostic agents, radiopaque agents, cryoprotective agents, perfumes insect repellants, hair dyes, antiscarring agents, sun screens, melanin-stimulating agents, antisecretory agents, depilatories, hair restorers, wrinkle-reducing agents, emollients, rubifacients, and cosmetic agents.

3. The method of claim 1 wherein said pharmacologically active agent is selected from the group consisting of: NDGA (nordihydroguaiaretic acid), VP-16 (epipodophyllotoxin beta-D ethylidene glucopyranoside—etoposide), VM-26 (epipodophyllotoxin beta-D thenylidene glucopyranoside—teniposide), 4'demethyl epipodophyllotoxin, diethylstilbestrol, dithranol, cyclophosphamide, mitomycin, daunomycin, platinum cis-diamine-dichloride, adriamycin, allopurinol, 5-fluorouracil, methotrexate; haloprogin, iodochloro, miconazole nitrate, tolnaftate, thiabendazole, chloroxine, amphotericin, candicin, fungimycin, nystatin, chlordantoin, clotrimazole, ethonam nitrate, miconazole nitrate, pyrrolnitrin, fezatione, ticlatone, tolnaftate, triacetin, dithiocarbamate, thiourea, thiocyantes, aromatic carboxylic acids and the amides thereof, benzoic acid, salicylic acid amide and anilide; aromatic sulfides, polysulfides, and sulfoxides, 5,5-dichloro-2,2-dihydroxydiphenylsulfide; quaternary ammonia and phosphonium compounds, decamethylene-bis-(4-thio-pyridine-methyl-tosylate, 8-hydroxyquinoline sulfate, halogenated quinolines, 7-iodo-8-hydroxyquinoline-5-sulfonic acid, 5-chloro-7-iodo-8-hydroxyquinoline, 5-chloro-8-hydroxy-quinoline, 5,7-dichloro-8-hydroxyquinaldine, 5,7-diiodo-8-hydroxyquinoline, decamethylene-bis (4-amino-quinaldium chloride); benzothiazole derivates, (2-dimethylamino-6-(beta-diaminoethoxy)-benzothiazole dihydrochloride; imidazole derivatives, 1-(o-chloro-alpha-alpha-diphenylbenzyl)-imidazole, 1-[o,p-dichloro-beta-(o,p-dichlorobenzyloxy)-phenethylimidazole], 2-phenylbenzimidazole, 2-furfurylbenzimidazole, 3,5-dibenzyltetrahydro-1,3,5-thiadizine-2-thione; 5-nitro-2-furfuryl-3-chloropropionate; quinones, tetrachloro-p-benzoquinone, 1,4-naphthoquinone, phenanthraquinone; sulfonamides and sulfones; aromatic diamidines, 2-hydroxystilbamidine, diamidinodiphenylamine; dioctyl sodium sulfosuccinate, haloprogin, miconazole nitrate, potassium sorbate, alkali and alkaline earth metal propionates, lauryl sulfate; sulfonomides, penicillins, cephalosporins, penicillinase, lincomycins, vancomycins, tetracylines, chloramphenicols, streptomycins, gramicidin, neomycin, polymyxin beta sulfate, tetracycline, benzethonium chloride, gentamicin sulfate, nitrofurazone, benzalkonium chloride, hexylresorcinol, chloroxylenol, cloflucarban, triclocarban, triclosan; glacial acetic acid, calcium pantothenate, lactic acid, cantharidin, podophyllin; acyclovir, benzalkonium chloride, alcohol, anhydrous glycerin, benzocaine, camphor, carbamide peroxide, lanolin, menthol, petrolatum, urea, idoxuridine, amantadine, methisazone, cytarabine, interferons, chloroform, ether, bacillus calmette-guerin, levamisole; benzoyl peroxide, resorcinol monoacetate, azelaic acid, adipic acid, C8 and C10-13 aliphatic dicarboxylic acids, sulfur, povidone-iodine, salicylic acid, fluocinolone acetonide, para-aminobenzoic acid sodium thiosulfate, meclocyline sulfosalicylate, sodium sulfacetamide, sulfurated lime; saponated cresol, menthol, mercury oleate, anthralin, methotrexate; N,N-dimethyl aspartic acid; N-N-dimethyl glutamic acid, antipyrine, camphor, eugenol, eucalyptol, thymol, allyl isothiocyanate (mustard oil, capsicum preparations, histamine dihydrochloride, methyl nicotinate, turpentine oil, diphenhydramine hydrochloride, phenyltoloxamine dihydrogen citrate, pyrilamine maleate, and tripelennamine hydrochloride; and the systemically hydrolyzable ethers and esters of all the foregoing.

4. The method according to claim 1 wherein the pharmacologically active agent and the zinc containing compound are present in approximately equimolar amounts.

5. The method according to claim 1 wherein the concentration of zinc-containing compound is less than about 35%.

6. The method according to claim 1 wherein the water-soluble zinc-containing compound dissociates to provide ionic zinc in the composition.

7. The method of claim 1 wherein said zinc-containing compound is a zinc salt.

8. The method according to claim 7 wherein the zinc salt is selected from the group consisting of zinc halide, zinc sulfate, zinc nitrate, zinc acetate and zinc stearate.

9. The method according to claim 7 wherein the zinc salt is zinc chloride.

10. A method of enhancing the skin and mucous membrane penetration and retention of a pharmacologically active agent comprising the topical application to the skin of a composition comprising said pharmacologically active agent and an effective penetrating and retaining amount of a zinc salt which acts to reduce the transdermal flux through the skin and mucous membrane of the pharmacologically active agent.

11. The method according to claim 10 wherein the zinc salt is zinc chloride.

12. A method of enhancing penetration of the skin and mucous membrane by a pharmacologically active agent selected from the group consisting of antineoplastic agents, immunopharmacological agents, steroids, antifungal agents, antiviral agents, antiparastic agents, pediculides, acne treatment compounds, antipsoriasis agents, leprosy agents, anethetic agents, analgesic agents, counter-irritants, antihistamines, allergy diagnostic agents, vitamins and nutrients, cosmetic agents and sunscreens comprising the application to the skin of a composition comprising the pharmacologically active agent and an effective penetrating and retaining amount of a water-soluble zinc-containing compound which acts to reduce the transdermal flux through the skin and mucous membrane of the pharmacologically active agent.

13. The method according to claim 12 wherein the water soluble zinc containing compound is a zinc salt.

14. The method according to claim 13 wherein the zinc salt is selected from the group consisting of zinc halide, zinc sulfate, zinc nitrate, zinc acetate, and zinc stearate.

15. A method of enhancing penetration of the skin and mucous membrane by a pharmacologically active agent other than erythromycin and retention of said pharmacologically active agent therein comprising the application to the skin of a composition comprising said pharmacologically active agent other than erythromycin and an effective penetrating and retaining amount of a water-soluble zinc-containing compound which acts to reduce the transdermal flux through the skin and mucous membrane of the pharmacologically active agent.

16. The method according to claim 15 wherein the zinc-containing compound is a zinc salt.

17. A method of enhancing penetration and retention of the skin and mucous membrane by a pharmacologically active agent selected from the group consisting of triamcinolone acetonide, clotrimazole, miconazole and salts thereof, salicylic acid and 5-fluorouracil composition the application to the skin of a composition comprising said pharmacologically active agent and an effective penetrating and retaining amount of a water-soluble zinc-containing compound which acts to reduce the transdermal flux through the skin and mucous membrane of the pharmacologically active agent.

18. A method of enhancing penetration and retention of the skin and mucous membrane by nordihydroguaiaretic acid comprising the application to the skin of a composition comprising said nordihydroguaiaretic acid and an effective penetrating and retraining amount of a water-soluble zinc-containing compound which acts to reduce the transdermal flux through the skin and mucous membrane of nordihydroguaiaretic acid.

19. A method of enhancing penetration and retention of the skin and mucous membrane by a pharmacologically active agent selected from the group consisting of retinoids and vitamin A comprising the application to the skin of a composition comprising said pharmacologically active agent and an effective penetrating and retaining amount of a water-soluble zinc-containing compound which acts to reduce the transdermal flux through the skin and mucous membrane of the pharmacologically active agent.

20. A method of enhancing penetration and retention of the skin and mucous membrane by acyclovir comprising the application to the skin of a composition comprising said acyclovir and an effective penetrating and retaining amount of a water-soluble zinc-containing compound which acts to reduce the transdermal flux through the skin and mucous membrane of acyclovir.

21. A method of enhancing penetration and retention of the skin and mucous membrane by dapsone comprising the application to the skin of a composition comprising said dapsone and an effective penetrating and retaining amount of a water-soluble zinc-containing compound which acts to reduce the transdermal flux through the skin and mucous membrane of dapsone.

22. A method of enhancing penetration and retention of the skin and mucous membrane by hydrocortisone comprising the application to the skin of a composition comprising said hydrocortisone and an effective penetrating and retaining amount of a water-soluble zinc-containing compound which acts to reduce the transdermal flux through the skin and mucous membrane of hydrocortisone.

23. A method of enhancing penetration and retention of the skin and mucous membrane by tetracycline comprising the application to the skin of a composition comprising said tetracycline and an effective penetrating and retaining amount of a water-soluble zinc-containing compound which acts to reduce the transdermal flux through the skin and mucous membrane of tetracycline.

24. A method of enhancing penetration and retention of the skin and mucous membrane by urea comprising the application to the skin of a composition comprising said urea and an effective penetrating and retaining amount of a water-soluble zinc-through containing compound which acts to reduce the transdermal flux through the skin and mucous membrane of urea.

25. A method of enhancing penetration and retention of the skin and mucous membrane by methotrexate comprising the application to the skin of a composition comprising said methotrexate and an effective penetrating and retaining amount of a water-soluble zinc-containing compound which acts to reduce the transdermal flux through the skin and mucous membrane of methotrexate.

26. A method of enhancing penetration and retention of the skin and mucous membrane by an antiviral agent comprising the application to the skin of a composition comprising said antiviral agent and an effective penetrating and retaining amount of a water-soluble zinc-containing compound which acts to reduce the transdermal flux through the skin and mucous membrane of the antiviral agent.

27. A method of enhancing penetration and retention of the skin and mucous membrane by a wrinkle reducing agent comprising the application to the skin of a composition comprising said wrinkle reducing agent and an effective penetrating and retaining amount of a water-soluble zinc-containing compound which acts to reduce the transdermal flux through the skin and mucous membrane of the wrinkle reducing agent.

28. A method enhancing penetration and retention of the skin and mucous membrane by an antifungal agent comprising the application to the skin of a composition comprising said antifungal agent and an effective penetrating and retaining amount of a water-soluble zinc-containing compound which acts to reduce the transdermal flux through the skin and mucous membrane of the antifungal agent.

29. A method of enhancing penetration and retention of the skin and mucous membrane by an antipsoriasis agent comprising the application to the skin of a composition comprising said antipsoriasis agent and an effective penetrating and retaining amount of a water-soluble zinc-containing compound which acts to reduce the transdermal flux through the skin and mucous membrane of the antipsoriasis agent.

30. A method of enhancing penetration and retention of the skin and mucous membrane by an antiinflammatory agent comprising the application to the skin of a composition comprising said antiinflammatory agent and an effective penetrating and retaining amount of a water-soluble zinc-containing compound which acts to reduce the transdermal flux through the skin and mucous membrane of the antiinflammatory agent.

* * * * *